United States Patent [19]

Batcho et al.

[11] 4,256,641

[45] Mar. 17, 1981

[54] NOVEL SYNTHESES OF TRYPTOPHANS

[75] Inventors: Andrew D. Batcho, North Caldwell; Urs O. Hengartner, Roseland; Willy Leimgruber; Montclair; John W. Scott, Upper Montclair; Donald Valentine, Jr., Highland Park, all of N.J.

[73] Assignee: Hoffmann-La Roche Inc., Nutley, N.J.

[21] Appl. No.: 62,214

[22] Filed: Jul. 30, 1979

Related U.S. Application Data

[62] Division of Ser. No. 965,549, Dec. 1, 1978, abandoned, which is a division of Ser. No. 849,734, Nov. 9, 1977, Pat. No. 4,140,697, which is a division of Ser. No. 698,573, Jun. 22, 1976, Pat. No. 4,073,795.

[51] Int. Cl.$^3$ .................................... C07D 209/20
[52] U.S. Cl. .................... 260/326.14 T; 260/319.1; 260/326.13 B; 260/326.14 T; 260/326.14 R; 260/326.16; 260/326.4; 260/404.24; 260/410.9 R; 568/425; 568/441; 426/540; 560/21; 560/22; 564/342; 564/344; 564/345
[58] Field of Search ............... 260/326.13 B, 326.14 T

[56] References Cited

U.S. PATENT DOCUMENTS

| | | | |
|---|---|---|---|
| 2,380,479 | 7/1945 | Stiller | 260/326.14 T |
| 3,953,442 | 4/1976 | Demarne | 260/326.15 |
| 4,073,795 | 2/1978 | Batcho et al. | 260/326.13 B |
| 4,087,444 | 5/1978 | Flaugh et al. | 260/326.13 B |
| 4,140,697 | 2/1979 | Batcho et al. | 260/326.13 B |

FOREIGN PATENT DOCUMENTS 2002067 10/1969 France.
1184538 3/1970 United Kingdom.

OTHER PUBLICATIONS

Hellmann et al., Annalin, vol. 361, pp. 175–179 (1960).
Aboskalova et al., J. Org. Chem. USSR, vol. 9, pp. 1062–1066 (1973).
Tamabe, Derwent Abs. 73311x, 5/9/73.

*Primary Examiner*—Mary C. Lee
*Attorney, Agent, or Firm*—Jon S. Saxe; Bernard S. Leon; George W. Johnston

[57] ABSTRACT

The preparation of racemic and optically pure tryptophans is described. The D-enantiomers of the 6-substituted compounds possess a potent sweetening capability. Novel intermediates are also disclosed.

5 Claims, No Drawings

NOVEL SYNTHESES OF TRYPTOPHANS

This is a division of application Ser. No. 965,549, filed Dec. 1, 1978, now abandoned, which in turn is a division of Ser. No. 849,734, filed Nov. 9, 1977, now U.S. Pat. No. 4,140,697, which in turn is a division of Ser. No. 698,573, filed June 22, 1976, now U.S. Pat. No. 4,073,795.

BACKGROUND OF THE INVENTION

Tryptophan, α-amino-β-indolepropionic acid, is an amino acid originally isolated from enzymatic digests of proteins. Tryptophan can be obtained by extraction, fermentation or chemical synthesis. Extraction is difficult because tryptophan is easily destroyed during acid hydrolysis of proteins, and racemization occurs on alkaline hydrolysis. Fermentative methods for tryptophan production from anthranilic acid or indole have been examined. The synthetic methods are generally of two types (1) syntheses in which the alanyl residue is added to a preformed indole and (2) syntheses in which the indole portion of the molecule is formed late in the sequence. The latter route is preferable, from an industrial point of view, because the indoles are costly raw materials. Furthermore, the latter syntheses involve a minimum of conversions during which the chemically sensitive indole nucleus can be destroyed. On the other hand, the indole formation usually involves cyclization into an aromatic ring leading to mixtures of isomers. The formation of isomers is particularly acute in the case of 4- and 6-substituted tryptophans.

The instant invention provides a means for the obtention, in high yield, of racemic and optically pure tryptophans, the D-enantiomers of which have potential value as non-nutritive sweeters.

Numerous substances have been proposed and/or used as non-nutritive sweetening agents, affording the consumer ingesting the same a sense of sweetness at least desirably comparable to that obtained with natural sugar, but without caloric effect. Such substances are necessary for some persons in order to limit intake of the natural sugars and thereby to control various health conditions, including diabetes. Many of these substances, however, have severe disadvantages. The most frequently encountered disadvantages are a bitter aftertaste and toxic side effects at rates not substantially different from those at which the sweetening effect is obtained. Only two classes of non-nutritive sweetening substances are used to any extent: saccharin-type compounds and cyclamate-type compounds. Both classes have the typical disadvantage of a bitter aftertaste; and in addition, cyclamate-type compounds have only limited activity.

Among the various categories of chemicals which have been evaluated for sweetening effect are the amino acids. A recent publication, Vuataz et al., Experientia, Vol. XXI, pages 692-694, inclusive (1965), reports the evaluation of a number of amino acids, the enantiomorphs being evaluated separately where available. The report shows that while a number of amino acids are sweet in the D form, this is not an absolute correlation. Furthermore, despite the sweet taste of the D-enantiomorph of a given amino acid, the L-enantiomorph of the same amino acid may be bitter. Resolution of the two enantiomorphs of a given amino acid is often difficult. For these various reasons, despite the contribution of Vuataz et al., no amino acid is being used in the sweetening art.

Moreover, throughout the sweetening art, it is well known that there is no correlation between structure and activity, as even relatively small changes in chemical structure often destroy activity.

In recent years the commercially-available synthetic sweetners, saccharin and cyclamate, have encountered some difficulties in toxicological studies. Aftertaste problems have also plagued these products. It has been evident, therefore, that a need exists for new sweetening agents. This need has been met, in part, by the new sweetener 1-aspartyl-1-phenylalanine methyl ester (Aspartame ®), but this dipeptide ester has shown instability under some conditions.

It has recently been discovered that certain substituted tryptophan compounds, in their D form, exhibit a sweet taste of a marked degree, at rates below rates at which any undesirable side effect may be noted. See U.S. Pat. No. 3,899,592 to Suarez et al., the disclosure of which is incorporated herein by reference.

Although it has been found that d,l-tryptophan has a sweetening capability, it is the d-enantiomorph that is the active moiety. Resolution of the d,l-mixture lessens the amount of substance needed for sweetening. Moreover, due to the fact that typically only the l-enantiomorph of amino acids is metabolized by the mammalian body, usage of the d-enantiomorph alone, may be preferred to preclude any opportunity for the mammalian body to incorporate the substance. When, for these or any other reason, it is desired to employ only the d-enantiomorph, resolution of the racemic mixture can be achieved in procedures known in the prior art for the resolution of unsubstituted tryptophan. Three such procedures are discussed and exemplified in detail in Chemistry of the Amino acids, Greenstein et al., vol. 3, page 2341 and following (John Wiley and Sons, Inc., New York, 1961), particular attention is directed to the first two of these (illustrative procedure 39-5 and illustrative procedure 39-6).

It is an object of the instant invention to prepare the aforementioned tryptophans either in the d,l- or the optically active form.

SUMMARY OF THE INVENTION

Compounds of the formula:

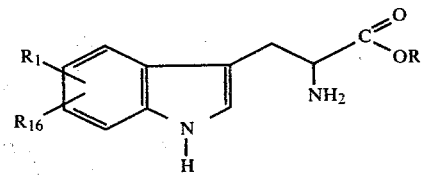

are prepared by treating a compound of the formula:

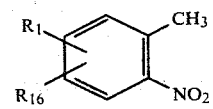

wherein $R_1$ and $R_{16}$ are hydrogen, lower alkyl or halogen, trihalomethyl, hydroxy, lower alkoxy, aralkyloxy and amino; in accordance with the following scheme:

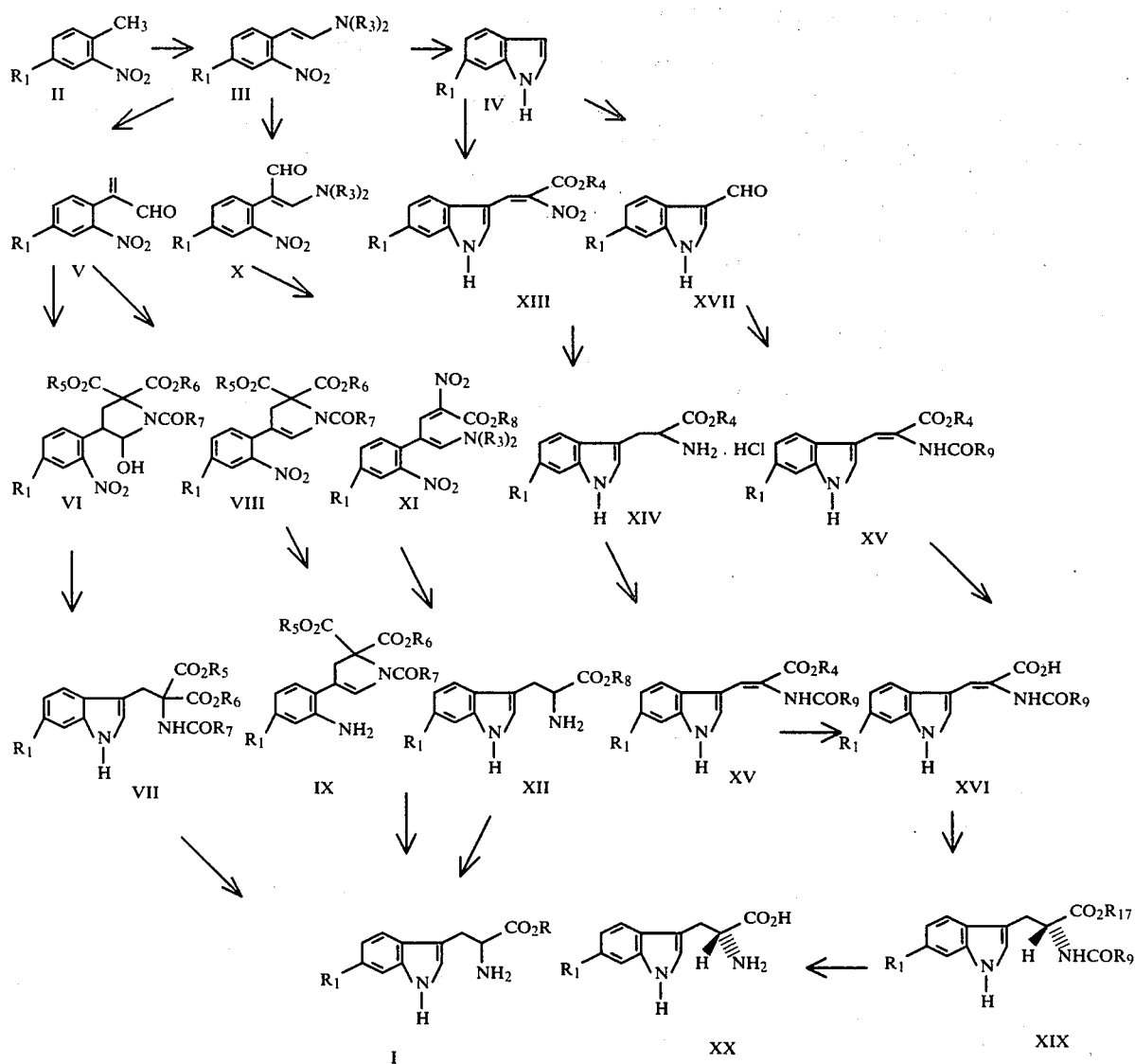

wherein R is hydrogen or lower alkyl; $R_3$ is lower alkyl or lower alkylene; $R_4$, and $R_8$ are lower alkyl or aryl; $R_5$ and $R_6$ are lower alkyl or hydrogen; $R_7$ and $R_9$ are lower alkyl, aryl, hydrogen, halo-lower alkyl or lower alkoxy.

The term "alkyl" as used herein, connotes straight or branched chain saturated hydrocarbon groups containing from 1 to 20 carbon atoms. The term "lower alkyl" connotes the above hydrocarbon groups containing from 1–6 carbon atoms. Typical lower alkyl groups are methyl, ethyl, propyl, isopropyl and the like. The term "halogen" connotes all four halogens, i.e., chlorine, bromine, fluorine and iodine. The term "lower alkylene" denotes alkylene groups of 1–6 carbon atoms such as ethylene, propylene, butylene and the like. The term "lower alkanol" connotes alkanols having 1–6 carbon atoms. The term "lower alkoxide" connotes an alkoxide having 1 to 6 carbon atoms. The term "lower acyl" connotes an alkanoyl group derived from an aliphatic carboxylic acid. Typical lower acyl groups are formyl, acetyl, propionyl and the like. The term "amino" connotes lower alkyl, mono-, di-, or tri-substituted amines. Typical amino groups are methylamino, ethylamino, diethylamino and the like. The term "aryl" connotes phenyl or phenyl bearing one or more substituents such as halogen, lower alkyl, lower alkoxy, nitroamino, lower alkylamino, and di-lower alkylamino. As used in this application, a tapered line ( ▲ ) indicates a substituent above the plane of the paper, a dashed line (≡) indicates a substituent below the plane of the paper.

In accordance with the present invention, compound II is treated with a formamide acetal of the formula:

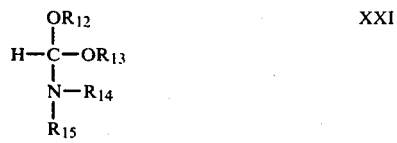

wherein $R_{12}$ and $R_{13}$ are lower alkyl, $R_{14}$ and $R_{15}$ are lower alkyl and may be taken together to form lower alkylene; to form compound III having the formula:

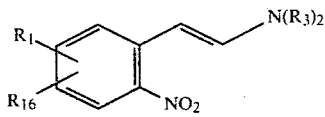   III wherein $R_1$, and $R_{16}$ are as defined above;

$R_3$ is lower alkyl or lower alkylene. Typical formamide acetals are, e.g., N,N-dimethylformamide diethyl acetal, N,N-dimethylformamide dimethyl acetal, N-formylpyrrolidine dimethyl acetal, 2-dimethylamino-1,3-dioxolane, N-formylpiperidine dimethyl acetal, N,N-dimethylformamide dibenzylacetal, N,N-dimethylformamide dicyclohexylacetal, dimethylformamide di-isopropyl acetal and the like. The formation of compound III from compound II is accomplished by heating the latter in the presence of the aforementioned formamide acetals at a temperature ranging from about 130° C. to about 160° C. In general, compound III is formed from compound II in accordance with the procedures set forth in U.S. Pat. No. 3,732,245 to Batcho et al. The Batcho et al. patent is incorporated herein by reference.

One aspect of this invention involves treating compound III with an acid halide and dialkylformamide (Vilsmeier formylation) to form a compound of the formula:

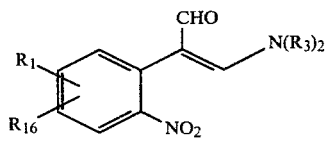   X wherein $R_1$, $R_3$ and $R_{16}$ are as defined above. Compounds where $R_1$ and $R_{16}$ are hydrogen and $R_3$ is methyl are known. The remaining compounds of formula X are novel and form a part of this invention. The acid halide-dialkylformamide treatment is carried out at a temperature of from 0° C. to 20° C. and then followed by treatment with base and heating at a temperature of from about 20° C. to about 100° C. The reaction is carried out in the presence of an aprotic solvent such as diethylether, methylenechloride, dichloroethane, pyridine and the like or with an excess of dimethylformamide (DMF).

The acid halides generally employed are compounds such as $POCl_3$, $SOCl_2$, $ClCO_2C_2H_5$ and $COCl_2$. Although the acid chlorides have been mentioned specifically, the bromides and iodides may be used as well. The amount of acid halide employed ranges from about 1 mole to about 5 moles per mole of compound III. The amount of dialkylformamide employed ranges from about 1 mole to 20 moles per mole of compound III. The reaction mixture is then treated with base and heated at a temperature of from 20° C. to about 100° C. to effect the formation of compound X. Sufficient base is employed such that the reaction mixture has a pH of from about 4 to about 14. Inorganic or organic bases may be employed. Typical bases that are used are alkali or alkaline earth metal hydroxides or alkoxides. Ammonium hydroxides may also be employed. Other conventional organic bases may also be employed.

Compounds of formula X where $R_1$ is either halogen, particularly chlorine, or methyl are novel and constitute an aspect of the invention.

Compound X is then condensed with a lower alkyl nitroacetate preferably methyl nitroacetate in the presence of a lower alkyl carboxylic acid anhydride, particularly acetic anhydride to form a compound of the formula:

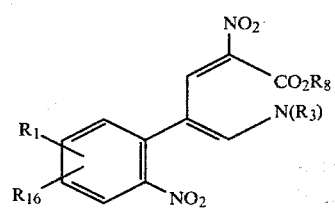   XI wherein $R_1$, $R_3$, $R_8$ and $R_{16}$ are as previously defined. Compound XI is novel and forms an additional aspect of this invention.

The condensation of compound X with a lower alkyl nitroacetate is conducted at a temperature of from about 50° C. to about 100° C. Although acetic anhydride is preferred, any lower alkyl carboxylic acid anhydride may be employed so long as said anhydride is liquid at the reaction temperature. The amount of lower alkyl nitroacetate employed varies from about 1 mole to about 10 moles per mole of compound X.

Compound XI is then transformed to a compound of the formula:

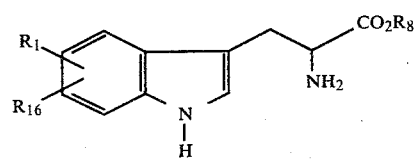   XII wherein $R_8$ is lower alkyl, preferably methyl, and $R_1$ and $R_{16}$ are as defined above; by catalytic reduction. The catalytic reduction is carried out at about room temperature and hydrogen pressures of from about 1 to about 200 atmospheres. Typical reduction catalysts that may be employed are the oxides of chromium, molybdenum, tungsten, platinum, palladium, rhodium, cobalt, nickel, and ruthenium. Raney nickel is particularly preferred. The catalyst may be utilized in the presence of an inert solvent such as a lower alkanol, e.g., methanol or ethanol, a hydrocarbon such as benzene or toluene or ethyl acetate. Solvents such as DMF and tetrahydrofuran (THF) may also be employed.

Compound XII is then transformed to compound I, where R is H, by conventional saponification procedures. Compound I is obtained as a racemic mixture. The D-form may be obtained by conventional resolution procedures.

Compound I may alternatively be prepared by treating compound III with a lower alkylamine, and formaldehyde in the presence of a mixed solvent system such as water, a lower alkanol and a lower alkyl monocarboxylic acid to form a compound of the formula:

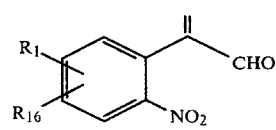   V wherein $R_1$ and $R_{16}$ are as previously defined. Compound V is novel and forms a further aspect of the invention. The transformation of compound III to compound V is conducted at a temperature of from −20° C. to about 50° C.

The lower alkylamine, preferably dimethylamine, is employed in an amount of from about 0.5 to about 5 moles per mole of compound III, preferably 1:1. The aldehyde, preferably formaldehyde, is employed in an amount ranging from about 1 mole to about 10 moles, preferably 3 moles, per mole of compound III. The preferred lower alkanol and monocarboxylic acid are methanol and acetic acid respectively.

Compound V may be transformed to a compound of the formula:

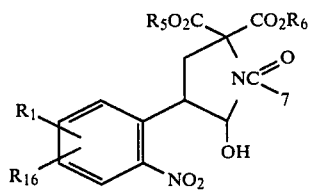
VI wherein $R_1$, $R_5$, $R_6$, and $R_{16}$ are as defined above, and $R_7$ is as defined above; by treating compound V with a lower acylamino malonate and a catalytic amount of base in the presence of a conventional solvent. Compound VI is novel and forms an additional aspect of this invention.

The transformation of compound V to compound VI is accomplished at a temperature ranging from about 0° C. to 25° C. The bases employed may be those set forth hereinabove. The solvents may be selected from lower alkanols, aliphatic and aromatic hydrocarbons such as benzene, toluene, xylene, hexane, octane and the like. A preferred acylamino malonate is formamidomalonate or acetamidomalonate.

Compound VI is then transformed to a compound of the formula:

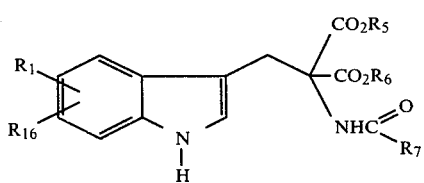
VII wherein $R_1$, $R_5$, $R_6$, $R_7$ and $R_{16}$ are as previously defined; by reduction. The reduction is carried out either catalytically or chemically, using the reducing agents set forth hereinabove, at a temperature ranging from about 0° C. to about 100° C. The reduction may be carried out in the same solvents as mentioned before, however, methanol is preferred. Subsequent to the reduction step and prior to the formation of compound VII, the reaction mixture is heated in the presence of an organic solvent to the reflux temperature of the solvent. Benzene is the preferred solvent. It has been discovered that prior to ring closure the following compound is formed:

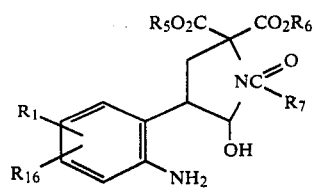
VIa wherein $R_1$, $R_5$, $R_6$, $R_7$ and $R_{16}$ are as defined above. Compound VII is then transformed to compound I by saponification and decarboxylation. This is accomplished by treating compound VII with a conventional strong base, e.g., sodium or potassium hydroxide followed by heating the reaction mixture to reflux in the presence of a lower alkyl monocarboxylic acid, preferably acetic acid. When $R_7$ is a substituent other than hydrogen, the decarboxylation step is followed by subsequent saponification to form compound I.

Compound VI may be dehydrated by catalytic amounts of strong acid to form a compound of the formula:

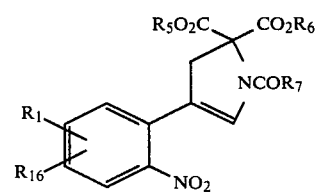
VIII wherein $R_1$, $R_5$, $R_6$, $R_7$ and $R_{16}$ are as previously defined. The dehydration is carried out at the reflux temperature of a conventional inert organic solvent. Benzene is the preferred solvent. Typical strong acids are methanesulfonic acid, p-toluenesulfonic acid, sulfuric acid, nitric acid, phosphoric acid and the like. In general, conventional acidic dehydrating agents can be employed.

Compound VIII is novel and forms still another aspect of this invention.

Compound VIII is transformed to compound IX, a compound of the formula:

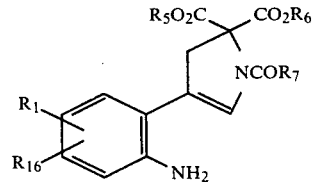
IX wherein $R_1$, $R_5$, $R_6$, $R_7$ and $R_{16}$ are as previously defined, by either chemical or catalytic reduction. Compound IX is novel and forms another aspect of this invention. The reduction may be accomplished employing the reducing agents and solvents set forth above. Preferred reducing agents for this transformation are sulfided platinum and palladium on a carbon support.

Compound IX is then transformed to compound I by conventional saponification and decarboxylation procedures. As an example compound IX may be transformed to compound I by treatment of the former with aqueous mineral acid at a temperature of about +100° C. Typical mineral acids that may be employed are HBr, HCl, H$_2$SO$_4$, and H$_3$PO$_4$. Aqueous HBr is preferred.

The foregoing procedures have illustrated the obtention of racemic tryptophans. Also within the scope of this invention are procedures for the obtention of optically pure D-tryptophans.

Compound III is transformed to a compound of the formula:

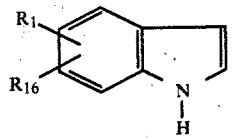
IV wherein R$_1$ and R$_{16}$ are as defined above, by either chemical or catalytic reduction means described hereinbefore.

Compound IV is then transformed to a compound of the formula:

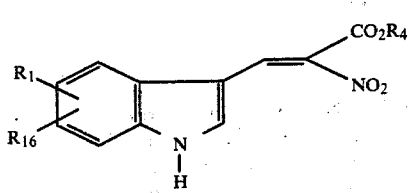
XIII wherein R$_1$, R$_4$ and R$_{16}$ are as previously defined. Compounds of formula XIII where R$_1$ and R$_{16}$ are hydrogen and R$_4$ is methyl or ethyl are known. The remaining compounds of formula XIII are novel and form a part of this invention. Compound XIII where R$_1$ is lower alkyl or halogen is novel and form a further aspect of this invention.

Compound XIII is formed by reacting compound IV, in the presence or absence of solvent, with an α-nitro-β-lower alkoxy acrylic acid lower alkyl ester. The reaction is carried out at a temperature ranging from about 0° C. to about 20° C. Typical solvents that may be employed are acetic anhydride, ethyl acetate and the polar solvents mentioned hereinbefore. The use of a solvent is preferred when the foregoing reaction is carried out on a large scale. The amount of α-nitro-β-lower alkoxy acrylic ester generally employed varies from about 1 mole to about 5 moles per mole of compound IV.

Compound XIII is reduced to form a compound of the formula:

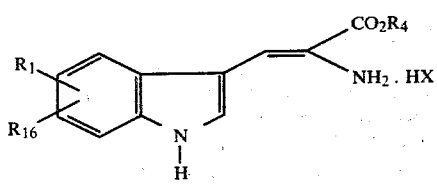
XIV wherein R$_1$, R$_4$ and R$_{16}$ are as previously defined and X is halogen. Compound XIV, where R$_1$ is lower alkyl or halogen, is novel and forms another aspect of this invention. Compound XIII is preferably reduced employing stannous chloride in the presence of an excess of HCl in a lower alkanol solvent, preferably methanol. The reduction is carried out at a temperature ranging from −30° C. to about 20° C. The HCl is employed in excess to prevent the precipitation of Sn(OH)$_2$ but to force the precipitation of compound XIV. The amount of SnCl$_2$ employed varies from about 3 moles to about 10 moles per mole of compound XIII.

Alternatively, the reduction of compound XIII to compound XIV can be accomplished at room temperature employing a metal catalyst. A preferred metal catalyst is partially deactivated platinum or palladium on a carbon support in a solvent such as ethyl acetate.

Compound XIV is then acylated to form a compound of the formula:

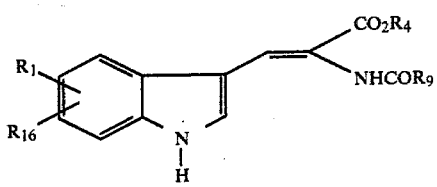
XV wherein R$_1$, R$_4$, R$_9$ and R$_{16}$ are as previously defined. Compounds of XV are known where R$_1$ and R$_{16}$ are hydrogen, R$_4$ is methyl and R$_9$ is methyl or phenyl.

The acylation of compound XIV to compound XV is carried out at a temperature of from about 0° C. to about 20° C. in the presence or absence of a conventional organic amine base. Although pyridine is a particularly preferred amine base, amine bases such as those mentioned hereinbefore may be employed. As acylation agents there may be employed any carboxylic acid halide or carboxylic acid anhydride. Typically employed are acylating agents such as benzoyl chloride, benzyl chloroformate, formic acetic anhydride, acetic anhydride, acetyl chloride, benzoic anhydride, chloroacetic acid anhydride and the like.

Compound XV is then saponified according to conventional procedures as set forth hereinabove to form a compound of the formula:

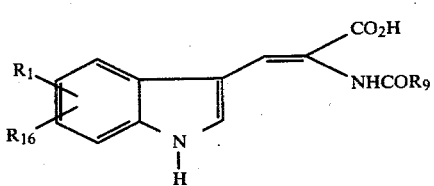
XVI wherein R$_1$, R$_9$ and R$_{16}$ are as previously defined. Compound XVI, where R$_1$ is lower alkyl or halogen, is novel and constitutes a further aspect of this invention.

Compound XVI is asymmetrically hydrogenated to form a compound of the formula:

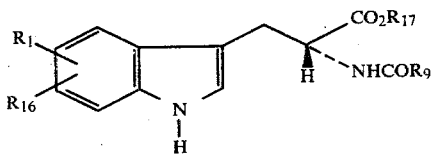
XIX wherein R$_1$, R$_9$ and R$_{16}$ are as previously defined, and R$_{17}$ is hydrogen, ammonium or lower alkyl ammonium.

The preparation of compound XIX from compound XVI is carried out in the presence of a soluble coordination complex of a rhodium(I) compound and a chiral tertiary phosphine. The complex is formed by reacting the rhodium compound with the tertiary phosphine where the P/Rh ratio is about 2:1 to about 10:1.

The source of rhodium is not critical and may be any compound that is convenient. Typical rhodium sources may be selected from μ,μ'-dichloro-bis-[1,5-cyclooctadiene rhodium(I)], hydrated rhodium trichloride, hydrated rhodium tribromide, (μ,μ'-dichlorobis-[bis-(olefin)rhodium(I)] wherein the olefin may be ethylene, propylene, cyclooctene, etc.; [rhodium(1,5-hexadiene)-Cl]₂, and [rhodium(bicyclo-2,2,1-hepta-2,5-diene)-Cl]₂.

The tertiary chiral phosphines utilized in the instant invention may be selected from the following compounds having the formula:

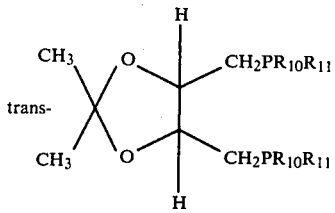
XXI wherein $R_{10}$ is aryl or substituted aryl wherein the substituents are selected from phenyl, tolyl, xylyl, mesityl, phenyl, benzyl, methoxyphenyl, chlorophenyl, ethylphenyl, cyclohexylphenyl, $R_{11}$ may be aryl or lower alkyl, wherein said lower alkyl is as previously defined; when $R_{10}$ and $R_{11}$ are both phenyl, the above compound XXI is designated as chiral trans-4,5-bis-(diphenylphosphinomethyl)-2,2-dimethyl-1,3-dioxolane (DIOP);

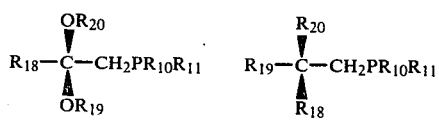
XXII wherein $R_{10}$ and $R_{11}$ are as defined above; $R_{18}$ and $R_{19}$ may be aryl or substituted aryl, hydrogen, alkyl, hydroxyalkyl, aminoalkyl or perfluoroalkyl, with the proviso that $R_{18}$ and $R_{19}$ must be different, and $R_{20}$ may be hydrogen, alkyl, aryl or substituted aryl.

When using DIOP as the phosphine, it has now been found that the optical yield of the hydrogenation is dependent on the position and number of substituents attached to the phenyl ring. Typical substituents, in addition to phenyl, found to be particularly useful are 3-methylphenyl, 4-methylphenyl, 3,5-dimethylphenyl, 3,4-dimethylphenyl, 2-methoxyphenyl, 3-methoxyphenyl, and 3-chlorophenyl. Excellent optical yields have been obtained when $R_{10}$ and $R_{11}$ of compound XXII are 3,5-dimethylphenyl.

The asymmetric hydrogenation is carried out at a temperature varying from about −70° C. to about 150° C. preferably −30° C. to about 50° C. and under a hydrogen pressure varying from about 2 psi to 500 psi, preferably about 2–100 psi. The product can be recrystallized from ammonia or a lower alkylamine. This procedure results in an enantiomeric excess of the D-isomer of about 99%. Compound XIX, where $R_1$ is lower alkyl or halogen, is novel.

Although the D-form is illustrated above, it is to be understood that the L-form can be produced by the same process depending upon the phosphine employed.

Compound XIX is acid hydrolyzed under reflux to form a compound of the formula:

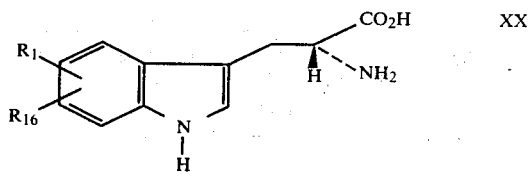
XX wherein $R_1$ and $R_{16}$ are as previously defined. The hydrolysis is carried out in a conventional manner employing acids such as HCl, HBr, $H_3PO_4$, p-toluenesulfonic acid and methanesulfonic acid.

Compound XV may also be subjected to catalytic asymmetric hydrogenation as described hereinbefore to form a compound of the formula:

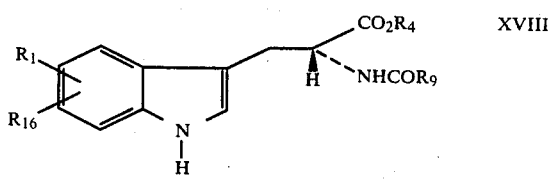
XVIII wherein $R_1$, $R_4$, $R_9$ and $R_{16}$ are as previously defined, depending on the nature of $R_4$ and $R_9$ the solubility of the optically active D- or L-enantiomer is considerably less than the racemate in a given solvent mixture of a lower alkanol and water, thus eliminating the optical purification step. In particular, the catalytic asymmetric hydrogenation of α-acetamido-6-methyl-3-indoleacrylic acid ethyl ester with a rhodium (I) compound and m-tolyldiop in a 9:1 methanol-water solution, results in the formed D-N-acetyl-6-methyltryptophan ethylester precipitating from the reaction mixture in 70% yield and 99.8% optical purity. Compound XVIII is then transformed to compound XX by acid hydrolysis in accordance with the procedure for transforming compound XIX to compound XX.

Alternatively compound IV may be treated with an acid halide and dialkylformamide to form a compound of the formula:

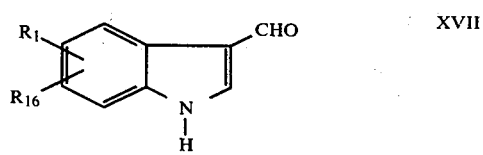
XVII wherein $R_1$, and $R_{16}$ are as previously defined. Compound XVII is prepared from compound IV in the same manner compound X was prepared from compound III which has been described hereinabove.

Compound XVII is then reacted with lower acylamidomalonic acid mono lower alkyl ester to form compound XV depicted hereabove.

The reaction to form compound XV from compound XVII is carried out at a temperature of from about 0° C. to about 50° C. in the presence of a lower carboxylic acid anhydride and a base. Particularly preferred is acetic anhydride/pyridine. The preferred lower lower acylamidomalonic acid mono lower alkyl ester is acetamidomalonic acid monoethyl ester.

Compound XV is then saponified according to conventional procedures set forth hereinabove to form compound XVI depicted hereinabove. Compound XVI is then transformed to compound XX in accordance with the procedures set forth hereinabove.

The following non-limiting examples illustrate the instant invention. All ratios are molar ratios and all temperatures are degrees Centigrade unless otherwise stated. The ether used is diethyl ether.

EXAMPLE 1

2-[2-Nitrophenyl]acrolein

A stirred mixture of 50 g. (0.365 mol) of 2-nitrotoluene, 56.0 g. (0.47 mol) of N,N-dimethylformamide dimethyl acetal and 200 ml. of dimethylformamide was heated under $N_2$ for 32 hr., raising the pot temperature gradually from 130° to 150° while the methanol formed during the reaction was removed by continuous distillation through a Vigreux column. Complete conversion of the starting 2-nitrotoluene was verified by nmr.-spectroscopy. The dark red solution of the enamine (compound III) was added to a mixture of 58 g. (0.52 mol) of 40% aqueous dimethylamine, 120 g. (1.48 mol) of 37% aqueous formaldehyde, 90 g. of acetic acid and 300 ml. of methanol at 4° over 1 hr. The mixture was stirred for 30 minutes at 4° and then the methanol was removed in vacuo. 1.5 l of water was added over 1 hr. at 10° and the suspension stirred at 4° for 2 hr. The crystalline precipitate was collected, washed with water and and dried to afford 55.8 g (86%) of product as brown crystals, m.p. 52.5°–54°. The analytical sample was prepared by recrystallization from ethanol, followed by evaporative distillation at 120°/0.1 mmHg; white crystals, m.p. 54.5°–56°.

Anal. calcd. for $C_9H_7NO_3$: C,61.02; H,3.98; N,7.91. Found: C,61.24; H,4.06; N,8.15.

EXAMPLE 2

2-[4-Methyl-2-nitrophenyl]acrolein

Following the procedure of Example 1, 2-nitro-1,4-dimethylbenzene (45.4 g, 0.30 mol) was reacted to give 46.0 g (80%) of 2-[4-methyl-2-nitrophenyl]acrolein, m.p. 58.5°–60° after recrystallization from ethanol. Analytical sample: white crystals, m.p. 59°–61°.

Anal. calcd. for $C_{10}H_9NO_3$: C,62.83; H,4.75; N,7.33. Found: C,62.91; H,4.63; N,7.35.

EXAMPLE 3

2-[4-Chloro-2-nitrophenyl]acrolein

Following the procedure of Example 1, 4-chloro-2-nitrotoluene (126 g, 0.734 mol) was reacted to give 144.3 g (93%) of 2-[4-chloro-2-nitrophenyl]acrolein, m.p. 87°–88° C. Analytical sample: white crystals, m.p. 89°–90.5°.

Anal. calcd. for $C_9H_6ClNO_3$: C,51.08; H,2.86; N,6.62; Cl,16.75. Found: C,51.29; H,3.02; N,6.63; Cl,16.83.

EXAMPLE 4

1-Formyl-5-hydroxy-4-[2-nitrophenyl]-pyrrolidine-2,2-dicarboxylic acid diethylester To a stirred, icebath-cooled mixture of 42.5 g. (0.24 mol) of acrolein of Example 1 and 50.4 g (0.25 mol) of diethyl formamidomalonate in 200 ml. of absolute ethanol was added, over 15 minutes, 4 ml. of a 1 M solution of sodium ethoxide in ethanol. The mixture was stirred at 5° for 1 hour as the Michael adduct crystallized out. After the suspension had been stored for 4 hours at −20°, the product was collected by filtration washed with ethanol (−60°) and dried to yield 82.4 g (90%) of off-white crystals, m.p. 109°–111°. The analytical sample was prepared by recrystallization from ethanol: white crystals, m.p. 113°–115°.

Anal. Calcd. for $C_{17}H_{20}N_2O_8$: C,53.68; H,5.30; N,7.36. Found: C,53.62, H,5.38; N,7.36.

EXAMPLE 5

1-Formyl-5-hydroxy-4-[4-methyl-2-nitrophenyl]-pyrrolidine-2,2-dicarboxylic acid diethyl ester Following the procedure of Example 4, the captioned compound was prepared. Base-catalyzed addition of 48.9 g. (0.24 mol) of diethyl formamidomalonate to 46.0 g (0.24 mol) of acrolein of Example 2 afforded 88.0 g (93%) of the captioned compound, m.p. 113°–114°. The analytical sample was prepared by recrystallization from ethanol: white crystals, m.p. 120°–122°;

Anal. Calcd. for $C_{18}H_{22}N_2O_8$: C,54.82; H,5.62; N,7.10. Found: C,54.98; H,5.56; N,7.10.

EXAMPLE 6

2-Formamido-3-(3-indolyl)-2-carbethoxypropionic acid ethyl ester 50.0 g (0.13 mol) of the compound of Example 4 in 500 ml. of methanol and 1 ml of acetic acid was hydrogenated in a rocking autoclave at room temperature and 200 psi in the presence of 6 g. of Raney nickel. After the hydrogen uptake (3 equivalents) was complete the filtered reaction mixture was concentrated in vacuo to a volume of 140 ml. Toluene (600 ml.) was added and the remaining methanol was removed by azeotropic distillation. The mixture was heated at reflux for an additional 30 minutes and then allowed to cool to room temperature. The precipitate was collected, washed with toluene and dried to yield 42.3 g (97%) of white crystals, m.p. 179°–180° (lit. m.p. 179°). The analytical sample was prepared by recrystallization from ethanol: m.p. 180°–181°.

Anal. Calcd. for $C_{17}H_{20}N_2O_5$: C,61.44; H,6.07; N,8.43. Found: C,61.51; H,6.10; N,8.39.

EXAMPLE 7

2-Formamido-3-(6-methyl-3-indolyl)-2-carbethoxypropionic acid ethyl ester 88.0 g (0.22 mol) of the compound of Example 5 in 800 ml of methanol and 1 ml of acetic acid was hydrogenated in the presence of 8 g of Raney nickel. The mixture was concentrated in vacuo and the solid residue was taken up in benzene (460 ml) and heated at reflux for 2 hours with constant removal of the water that was formed. Hexane (390 ml) was added and the mixture was allowed to stand at room temperature overnight. The precipitate was collected, washed with benzene-hexane (1:2) and dried to give 69.5 g (90%) of white crystals, m.p. 133°–134.5° (sinters at 113°). The analytical sample was prepared by recrystallization from benzene-hexane: m.p. 114°–116° (recrystallization from ethanol-water gave crystals with m.p. 135°–136°).

Anal. Calcd. for $C_{18}H_{22}N_2O_5$: C,62.42; H,6.40; N,8.09. Found: C,62.51; H,6.34; N,8.08.

EXAMPLE 8

Tryptophan

A mixture of 40 g (0.12 mol) of the compound of Example 6 and 24.0 g (0.60 mol) of sodium hydroxide in 240 ml. of water was heated at reflux for 18 hours. 48 ml of glacial acetic acid was added to the solution and heating was continued for an additional 8 hours. The suspension was allowed to stand at 0° overnight and the white precipitate was collected, washed with icecold water and dried to yield 24.7 g (100%) of crude product. Recrystallization from 80% aqueous acetic acid afforded, after drying at 100°/0.05 mmHg, 21.2 g (86%) of white crystals, m.p. 292° (dec.) (lit. m.p. 293°) which was identical with an authentic sample.

Anal. Calcd. for $C_{11}H_{12}N_2O_2$: C,64.69; H,5.92; N,13.72. Found: C,64.86; H,6.06; N,13.86.

EXAMPLE 9

6-Methyltryptophan 68.5 g (0.20 mol) of the compound of Example 7 was converted in the same manner to give 35.8 g (83%) of recrystallized product as white crystals, m.p. 298° (dec) (lit. m.p. 298°–300°) which was identical with an authentic sample.

Anal. Calcd. for $C_{12}H_{14}N_2O_2$: C,66.04; H,6.47; N,12.84. Found: C,66.22; H,6.52; N,12.95.

EXAMPLE 10

1-Acetyl-4-(4-chloro-2-nitrophenyl)-2,3-dihydro-1H-pyrrole-2,2-dicarboxylic acid diethyl ester A solution of 143.0 g (0.676 mol) of 2-(4-chloro-2-nitrophenyl) acrolein in 600 ml. of benzene was added over 1.5 hour to a stirred suspension of 148.5 g (0.684 mol) of diethyl acetamidomalonate and 0.80 g of sodium methoxide in 600 ml. of benzene. The Michael addition was complete after 30 minutes. 3.8 g of p-toluenesulfonic acid monohydrate was added and the mixture was heated at reflux for 40 minutes with constant removal of the water formed. The reaction mixture was washed with saturated sodium bicarbonate and brine. After drying with anhydrous NaSO$_4$, the orange solution was concentrated to yield 278.5 g, m.p. 90°–95°. Crystallization from ethanol (500 ml) gave 264.6 g (95%) of deep yellow crystals, m.p. 96°–98°. A sample was recrystallized again from ethanol: m.p. 96.5°–98°.

Anal. Calcd. for $C_{18}H_{19}N_2O_7Cl$: C,52.63; H,4.66; N,6.82; Cl, 8.63. Found: C,52.82; H,4.50; N,6.94; Cl 8.49.

EXAMPLE 11

1-Acetyl-4-(2-amino-4-chlorophenyl)-2,3-dihydro-1H-pyrrole-2,2-dicarboxylic acid diethylester A solution of 32.2 g (0.20 mol) of the compound of Example 10 in 300 ml of tetrahydrofuran and 700 ml of methanol was hydrogenated in the presence of 4 g of 5% sulfided platinum on carbon at room temperature and 1500 psi for 22 hours. The reaction mixture was concentrated and the solid residue (76 g) was recrystallized from ethanol (320 ml) to afford 61.4 g (81%) of light orange crystals, m.p. 151.5°–153°. The analytical sample was prepared by a second recrystallization from ethanol: white crystals, m.p. 152°–153.5°.

Anal. Calcd. for $C_{18}H_{21}N_2O_5Cl$: C,56.77; H,5.56; N,7.36; Cl, 9.31. Found: C,57.06, H,5.61; N,7.40; Cl, 9.43.

EXAMPLE 12

6-Chlorotryptophan

A mixture of 60 g (0.16 mol) of the compound of Example 11, and 450 ml. of 2 N aqueous HBr was heated under N$_2$ at 95° for 30 hours. The solution was concentrated in vacuo and the residual salt was taken up in 300 ml of water. The solution was brought to pH 5.5 with 4 N NaOH and the mixture was chilled in an icebath for 1 hour. The precipitate was collected, washed with cold water and dried to give 34.8 g of product. Crystallization from glacial acetic acid (360 ml.) afforded, after drying at 100°/0.2 mmHg, 30.8 g (82%) of white crystals, m.p. 280° (dec.) (lit. m.p. 285°–286°), which was identical with an authentic sample.

Anal. Calcd. for $C_{11}H_{11}N_2O_2Cl$: C,55.36; H,4.65; N,11.74; Cl,14.85. Found: C,55.62; H,4.66; N,11.91; Cl,14.78.

EXAMPLE 13

3-Dimethylamino-2-[4-chloro-2-nitrophenyl]acrolein

A stirred mixture of 53.8 g (0.31 mol) of 4-chloro-2-nitrotoluene, 50.0 g (0.42 mol) of N,N-dimethylformamide dimethyl acetal and 175 ml. of dimethylformamide was heated under N$_2$ for 22 hours at 135°, while the methanol formed was removed by continuous distillation through a 25-cm Vigreux distilling head. At the end of the reaction period the temperature was brought to 155°. The dark red solution of the chloro analog of compound III was then added at 10°–15° over 30 minutes to a mixture of 62 g (0.40 mol) of phosphorus oxychloride and 145 ml of dimethylformamide, (prepared by adding the acid chloride slowly at 15° to the dimethylformamide). The orange solution was stirred at room temperature for 1 hour. Then, 1 kg of ice was added, followed by a solution of 80 g (2.0 mol) of sodium hydroxide in 300 ml of water. The mixture was heated at 60° for 20 minutes and allowed to stand at room temperature overnight. The precipitate was collected, washed with water and dried to afford 73.1 g (92%) of product was orange crystals, m.p. 145°–147°. The analytical sample was prepared by recrystallization from benzene: light orange crystals, m.p. 146°–147.5°.

Anal. Calcd. for $C_{11}H_{11}N_2O_3Cl$: C,51.88; H,4.35; N,11.00; Cl,13.92. Found: C,51.86; H,4.43; N,10.87; Cl,13.84.

EXAMPLE 14

3-Dimethylamino-2-[2-nitrophenyl]acrolein

A mixture of 50.0 g (0.36 mol) of 2-nitrotoluene, 56.0 g (0.47 mol) of N,N-dimethylformamide dimethyl acetal and 190 ml of dimethylformamide was heated under N$_2$ for 22 hours at 140°–145°, while the methanol formed was continuously removed by distillation. The resulting solution of enamine III was added at 10°–15° over 30 minutes to a mixture of 71.3 g (0.46 mol) of phosphorus oxychloride and 165 ml. of dimethylformamide. After the mixture had been stirred for 1 hour at room temperature, 1.1 kg of ice was added, followed by a solution of 92 g (2.3 mol) of sodium hydroxide in 345 ml of water. The mixture was heated at 60° for 2 hours and then refrigerated overnight. The precipitate was collected, washed with water and dried to yield 65.0 g (81%) of product as orange crystals, m.p. 116°–118.5° (lit. m.p. 116°–119°). The analytical sample was prepared by recrystallization from benzene: m.p. 116.5°–118.5°.

Anal. Calcd. for $C_{11}H_{12}N_2O_3$: C,60.00; H, 5.49; N,12.72. Found: C,59.78; H,5.67; N,12.56.

EXAMPLE 15

3-Dimethylamino-2-[4-methyl-2-nitrophenyl]acrolein 50.0 g (0.33 mol) of 2-nitro-1,4-dimethylbenzene was reacted as in Example 14 affording 67.9 g (88%) of product as yellow-orange crystals, m.p. 117°–119°. The analytical sample was prepared by recrystallization from ethanol: m.p. 119°–121°.

Anal. Calcd. for $C_{12}H_{14}N_2O_3$: C,61.53; H,6.02; N,11.96. Found: C,61.68; H,5.83; N,12.02.

EXAMPLE 16

5-Dimethylamino-2-nitro-4-[4-chloro-2-nitrophenyl]-2,4-pentadienoic acid methyl ester A mixture of 73.1 g (0.29 mol) of the compound of Example 13, 34.0 g (0.29 mol) of methyl nitroacetate and 600 ml of acetic anhydride was stirred and heated at 90°–95° for 45 minutes. The reaction mixture was allowed to cool to room temperature and the crystalline product was collected by filtration. The filtrate was concentrated in vacuo and the residue was slurried with ether (200 ml.) and filtered. The combined materials were washed with ether and dried to give 91.0 g (89%) of red orange crystals, m.p. 193°–197°. Recrystallization from benzenedimethylformamide (6:1,1725 ml) afforded 78.8 g (77%) of product, m.p. 198°–200°.

Anal. Calcd. for $C_{14}H_{14}N_3O_6Cl$: C,47.27; H,3.97; N,11.81; Cl,9.97. Found: C,47.34; H,4.09; N,11,81; Cl,9.96.

EXAMPLE 17

5-Dimethylamio-2-nitro-4-[2-nitrophenyl]-2,4-pentadienoic acid methyl ester

A mixture of 63.0 g (0.29 mol) of the compound of Example 14 and 35.7 g (0.30 mol) of methyl nitroacetate in 600 ml. of acetic anhydride was heated at 85° for 2 hours. The resulting product was worked up and recrystallized from benzene-DMF (2:1) affording 74.9 g (81%) of product as red orange crystals, m.p. 211°–214°.

Anal. Calcd. for $C_{14}H_{15}N_3O_6$: C,52,33; H,4.71; N,13.08. Found: C,52.50; H,4.79; N,13.07.

EXAMPLE 18

5-Dimethylamino-2-nitro-4-[4-methyl-2-nitrophenyl]-2,4-pentadienoic acid methyl ester A mixture of 67.5 g (0.29 mol) of the compound of Example 15 and 34.3 g (0.29 mol) of methyl nitroacetate in 540 ml of acetic anhydride was heated at 60° for 2 hours. The product was worked up and recrystallized from benzene-DMF (3:1) affording 75.1 g (78%) of product as red orange crystals, m.p. 213°–215°.

Anal. Calcd. for $C_{15}H_{17}N_3O_6$: C,53.73; H,5.11; N,12.53. Found: C,53.93; H,4.99; N,12.65.

EXAMPLE 19

6-Chlorotryptophan

A mixture of 20.0 g (0.056 mol) of the compound of Example 16 and 8 g of Raney nickel in 250 ml. of methanol and 250 ml of tetrahydrofuran was hydrogenated in a rocking autoclave at 1500 psi for 22 hours. The filtered solution was concentrated and the crude 6-chlorotryptophan methyl ester (14.4 g, ca. 70% pure) was dissolved in 75 ml of methanol. 4.5 g of sodium hydroxide was added and the mixture was stirred at 50° for 3 hours. The brown solution was again concentrated and the solid residue taken up in 50 ml. of water. 125 ml of ethyl acetate was added and the two phase system was stirred while the aqueous layer was adjusted to pH 5.5 with acetic acid. The mixture was allowed to stand at 0° overnight. The precipitate was collected, washed with ethyl acetate (100 ml), ether (50 ml) and ice cold water (50 ml) and dried to give 8.8 g of crude product. GC-analysis of its tris-trimethylsilyl-derivative confirmed the absence of tryptophan. Recrystallization from glacial acetic acid yielded, after drying at 120°/0.1 mm, 7.80 g (58%) of off-white crystals, m.p. 278° (dec.) (lit. 285°–286°), which was identical with an authentic sample.

Anal. Calcd. for $C_{11}H_{11}N_2O_2Cl$: C,55.36; H,4.65; N,11.74; Cl,14.85. Found: C,55.45; H,4.60; N,11.64; Cl,14.87.

EXAMPLE 20

Tryptophan

Following the procedure of Example 19, 20 g (0.062 mol) of the product of Example 17 were hydrogenated and worked up to yield 7.98 g (63%) of recrystallized product, m.p. 291° (dec.) (lit. m.p. 293°), which was identical with an authentic sample.

Anal. Calcd. for $C_{11}H_{12}N_2O_2$: C,64.69; H,5.92; N,13.72. Found: 64.64; H,5.86; N,13.67.

EXAMPLE 21

6-Methyltryptophan 70 g (0.21 mol) of the product of Example 18 were hydrogenated and worked up as described above to yield 27.6 g (61%) of recrystallized product, m.p. 297° (dec.) (lit. m.p. 298°–300°) which was identical with an authentic sample.

Anal. Calcd. for $C_{12}H_{14}N_2O_2$: C,66.04; H,6.47; N,12.84. Found: C,66.08; H,6.62; N,12.88.

EXAMPLE 22

Nitroacetic acid methylester

A 22-1. three-necked flask, equipped with a thermometer, mechanical stirrer and dropping funnel provided with a calcium sulfate drying tube was charged with 3.445 l (36.5 moles) of acetic anhydride. The flask content was cooled to 0° and 417 ml (8.8 moles) of 90% nitric acid were added at 0° over 1 hour. Stirring was continued for 15 minutes at this temperature. The mixture was then cooled to −15° and 1.00 kg (8.61 moles) of methyl acetoacetate was added at this temperature over 2½ hours. The mixture was then brought to −35° and 1.9 ml of cencentrated sulfuric acid was dropwise added over 1 hour, while the temperature was kept between −38° and −32°. Stirring was continued for 30 minutes at this temperature. The yellow mixture was allowed to warm to room temperature over 2 hours. 3.445 l (85 moles) of methyl alcohol were added over 50 minutes with ice bath cooling, keeping the temperature at 25°–30°. The mixture was stirred at room temperature overnight and then 7.3 g of anhydrous sodium carbonate were added. The dropping funnel was replaced by a distilling head with condenser and the light volatile components distilled off in vacuo (16 mmHg, bath temperature 50°). The residual oil was distilled through a 10-cm. Vigreux column at 0.2 mmHg pressure and a bath temperature of 70°. After a small forerun, 746 g. (73%) of nitroacetic acid methylester were collected as a colorless, mobile oil, b.p. 45°/0.2 mmHg.

EXAMPLE 23

Alpha-nitro-beta-ethoxyacrylic acid methylester

A 12-1. three-necked flask, equipped with a thermometer, mechanical stirrer and a reflux condenser was charged under an atmosphere of nitrogen with 746 g (6.26 moles) of nitroacetic acid methylester, 1392 g (9.4 moles) of triethyl orthoformate and 1.92 l of acetic anhydride. The mixture was stirred and heated at reflux for 23 hours. The volatile components were distilled off first at atmospheric pressure (pot temperature up to 100° C., then at aspirator vacuum and finally at 0.17 mmHg (pot temperature up to 70°), leaving 926 g (84%) of crude alpha-nitro-beta-ethoxyacrylic acid methylester as an orange oil.

EXAMPLE 24

Alpha-nitro-6-chloro-3-indoleacrylic acid methylester

A 4-l. battery jar was charged with 641 g (4.23 moles) of 6-chloroindole, 926 g (5.3 moles) of crude (ca. 85% pure) alpha-nitro-beta-ethoxy acrylic acid methylester and 475 L g (4.65 moles) of acetic anhydride. The mixture was well stirred at room temperature for 45 hours to give a highly viscous suspension of an orange precipitate. 1.5 l of a mixture of benzene-ether-hexane 1:1:3 was added and the mixture stirred vigorously for 30 minutes. The product was collected by filtration, washed with 1.0 l of the same solvent mixture and dried at room temperature and 16 mmHg to constant weight to afford 600 g (51%) of product as orange crystals, m.p. 159°–160°.

EXAMPLE 25

Alpha-amino-6-chloro-3-indoleacrylic acid methylester hydrochloride

A 3-l. three-necked flask, equipped with a thermometer and a mechanical stirrer was charged with 316 g (1.4 moles) of stannous chloride dihydrate and a solution of 111 g (3 moles) of dry hydrogen chloride gas in 1 l. of methyl alcohol. The colorless solution was stirred and cooled to −30° in a dry ice-acetone bath. 112.3 g (0.40 moles) of alpha-nitro-6-chloro-3-indoleacrylic acid methylester was added in 4 equal portions over 1 hour, maintaining the temperature between −25° and −20°. After the addition was complete, the temperature was allowed to rise to −10° and stirring at this temperature was continued for 90 minutes. Then 500 ml. of ether was added to the yellow suspension, followed by addition of 500 ml of 12 N hydrochloric acid (concentrated), the temperature was kept below 5°. The mixture was then filtered through a Büchner funnel. The filter cake was washed with 1000 ml of methyl alcohol-9 N aqueous hydrochloric acid 1:1, precooled to −20°, and 400 ml of ether. The tan product was dried at 40°/0.1 mmHg for 8 hours and then at 20°/0.1 mmHg to constant weight to yield 103.4 g (90%) of crude product, m.p. 191° (dec.).

EXAMPLE 26

Alpha-acetamido-6-chloro-3-indoleacrylic acid methylester

A 2-l. three-necked flask, equipped with a thermometer, a mechanical stirrer and a dropping funnel was charged with 101.2 g (ca. 0.35 moles) of crude pulverized alpha-amino-6-chloro-3-indolearcylic acid methylester hydrochloride and 400 ml of acetic anhydride. The slurry was cooled to 15°. Then 32 g (0.40 moles) of pyridine was added with stirring over a 5 minute period, while the temperature was kept between 15° and 22°; after complete addition, virtually all starting hydrochloride went into solution. Stirring at 22° was continued for 20 minutes during which the product began to crystallize out. 200 ml of water was then added over 40 minutes, keeping the temperature at ca. 25°. Stirring at this temperature was continued for 1½ hours. 900 ml of water was then added over 5 minutes and the slurry stirred at room temperature for an additional hour. The precipitate was collected by suction filtration, washed with 750 ml of water and dried at 60° (constant weight) to afford 92.9 g (90%) of product, as yellow crystals, m.p. 202°–203.

EXAMPLE 27

Alpha-acetamido-6-chloro-3-indoleacrylic acid

A 2-l. three-necked flask, equipped with thermometer mechanical stirrer and reflux condenser was charged with 90.4 g (0.31 moles) of alpha-acetamido-6-chloro-3-indoleacrylic acid methylester, 200 ml (0.40 moles) of 2 N aqueous sodium hydroxide and 400 ml of methylalcohol. The mixture was stirred and heated at an internal temperature of 55°–58° for 90 minutes. 800 ml of distilled water was added and the brown slightly turbid solution filtered through a Büchner funnel. The clear filtrate was acidified with 90 ml (0.54 moles) of 6 N aqueous hydrochloric acid. The precipitate was collected on a Büchner funnel and washed with distilled water. The wet cake was transferred into flask and suspended in 180 ml of dimethylformamide and 600 ml of methyl alcohol. The mixture was heated on a steam bath to reflux until a brown, slightly turbid solution was formed. 6 g of charcoal was added and reflux was continued for 10 minutes. The hot mixture was quickly filtered through a bed of Celite. The deep yellow, clear filtrate was transferred into a 2-l. flask, equipped with reflux-condenser and dropping funnel and brought again to reflux under an atmosphere of nitrogen. 240 ml of distilled water was added over a 5 minute period while reflux was maintained. The miture was allowed to stand overnight under an atmosphere of nitrogen at room temperature. The product was collected by suction filtration, washed with methyl alcohol-water 1:1 and dried at 85°/0.5 mmHg, to constant weight to give 78.6 g (86%) of product, as yellow crystals, m.p. 255°.

EXAMPLE 28

Trans-beta-dimethylamino-4-methyl-2-nitrostyrene

A 12-l. three-necked flask, equipped with a thermometer, a mechanical stirrer and a 60 cm. vacuum-jacketed silvered column with glass helice packing connected to a total-condensation, variable take-off still head with receiver was charged under nitrogen with 675 g (4.46 moles) of 2-nitro-1,4-dimethylbenzene, 736 g (6.17 moles) of N,N-dimethyl formamide dimethyl acetal and 3.0 l of N,N-dimethylformamide. The mixture was stirred and heated with a heating mantle for 37 hours. The pot temperature was gradually raised from 130° to 144° while the formed methanol was removed by distillation. The fractionating column was replaced by a distilling head with condenser and receiver (cooled in a dry ice-acetone bath). The dimethylformamide was remove by distillation, first at aspirator vacuum and then at high vacuum (water bath 70°), giving a residue of 924 g (100%) of crude product as a dark red viscous oil. This material was poured into a beaker and mixed thoroughly with 640 ml of methyl alcohol. The mixture was stirred in an ice bath until the product crystallized in mass and was then refrigerated overnight. The precipitate was collected by suction filtration, washed with 320 ml of methyl alcohol and dried in vacuo at room temperature (constant weight) to afford 760 g (83%) of

EXAMPLE 29

6-Methylindole

A glass-lined rocking autoclave was charged with a solution of 300 g (1.45 moles) of trans-β-dimethylamino-4-methyl-2-nitrostyrene in 3 l of benzene and 15 g of 5% palladium on carbon. The autoclave was pressurized with 20 psi of hydrogen and rocked for 5 hours. The mixture was filtered through a bed of Celite, which was washed thoroughly with benzene. The filtrate was concentrated to half its volume and washed with 1 l of 0.25 N hydrochloric acid, 500 ml of saturated sodium bicarbonate and 500 ml of brine. The aqueous phases were backwashed with 500 ml of benzene and the combined organic phases were dried over sodium sulfate and concentrated. The residual dark brown oil was distilled at vacuo to afford 157.9 g (83%) of product as a light yellow oil, b.p. 80°-85°/0.05 mmHg, which solidified after seeding to a light yellow solid, m.p. 29°-30.5°.

EXAMPLE 30

6-Methyl-indole-3-carboxaldehyde

A 12-l. three-necked flask, equipped with a mechanical stirrer, a thermometer and a dropping funnel provided with a Drierite drying tube was charged with 610 ml (7.9 moles) of N,N-dimethylformamide. The flask was immersed in an ice bath and 217 g (1.42 moles) of phosphorus oxychloride was added at 5°-10° with stirring over 1 hour. The dropping funnel was rinsed with 20 ml of dimethylformamide and the light pink orange oil was stirred for further 10 minutes in the ice bath. Then a solution of 156 g (1.19 moles) of 6-methylindole in 156 ml of dimethylformamide was added at 5°-10° C. over a period of 1 hour. The ice bath was removed and the red orange solution was stirred for an additional hour, while the flask content warmed up to room temperature. At the end of the reaction period, 1.17 kg of crushed ice was added. The temperature fell to −10° and after a short time a light yellow slurry was formed. The reaction mixture was stirred for 1 hour, as the temperature came to 15°. Then a solution of 840 g (13.0 moles) of potassium hydroxide pellets (87% assay) in 2 l of water was added over 30 minutes, during which time the pot temperature rose to 50°. After the addition was complete, the dropping funnel was replaced by a reflux condenser and the orange solution was heated rapidly with stirring on a steam bath to 93° and kept at this temperature for 30 minutes. The mixture was allowed to stand at room temperature overnight. The precipitate was collected by suction filtration, washed with water and dried at 60° (constant weight) to give 186.5 g (98%) of product as orange crystals, m.p. 183°-186°.

EXAMPLE 31

Alpha-acetamido-6-methylindole-3-acrylic acid ethylester

A 3-l. three-necked flask, equipped with a mechanical stirrer, a thermometer and a dropping funnel with pressure-equalizing arm was charged with 100 g (0.63 mol) of 6-methylindole-3-carboxaldehyde, 119 g (0.63 mol) of acetamidomalonic acid monoethylester and 500 ml of pyridine. The mixture was stirred and kept at 15° with a cold water bath while 175 ml of acetic anhydride was added over 15 minutes. The yellow solution was stirred at room temperature for 3 hours. Then an additional portion of 36 g (0.19 mol) of acetamidomalonic acid monoethyl ester was added and stirring at room temperature was continued for 22 hours before 1 kg of ice was added. The temperature fell to −10° and the product began to precipitate. The suspension was stirred at room temperature for 5 hours and poured into 2 l of water. After 20 minutes, the precipitate was collected by suction filtration, washed with water and dried at 50° in an air oven overnight to afford 159.5 g (89%) of crude product as yellow crystals, m.p. 159°-162° (sinters at 75°).

EXAMPLE 32

Alpha-acetamido-6-methylindole-3-acrylic acid monohydrate 2-l. three-necked flask, equipped with a mechanical stirrer, a thermometer and a dropping funnel was charged with 159.5 g (0.56 mol) of crude alpha-acetamido-6-methylindole-3-acrylic acid ethylester and 475 ml of methanol. The mixture was heated in an oil bath to 50°. A solution of 66.8 g (1.67 mol) of sodium hydroxide in 320 ml of water was added over 3 minutes and the resulting brown solution was stirred at 50° for 45 minutes. The reaction mixture was cooled with an ice bath to 25° and 600 ml of 4 N hydrochloric acid was added over 20 minutes at 25°. The precipitate was collected on a Büchner funnel, washed with 900 ml of water and dried at 50° overnight and at 60°/0.5 mm for 3 hours. The beige solid (146 g) was dissolved in 1 l of methanol and 175 ml of dimethylformamide at reflux. 10 g of charcoal was added and reflux was continued for 10 minutes. The mixture was filtered through a bed of Celite and the clear brown solution was brought again to reflux. 425 ml of water was added over a 20 minute period, while reflux was maintained. The mixture was refrigerated for 3 hours. The product was collected by suction filtration, washed with 750 ml of 1:1 methanol—water and dried at 50° for 24 hours (const. weight) to yield 119.9 g (69%, based on 6-methylindole-3-carboxaldehyde of product as yellow crystals, m.p. 229° (dec.).

EXAMPLE 33

Ammonium salt of D-N-acetyl-6-methyltryptophan

A mixture of 300 g (1.09 mol) of alpha-acetamido-6-methylindole-3-acrylic acid monohydrate, 33 mg of $Rh_2(cyclooctadiene)_2Cl_2$, 74 mg of chiral trans-4,5-bis-(di-m-toylphosphinomethyl)-2,2-dimethyl-1,3-dioxolane(m-tolyldiop) and 2.4 l of oxygen free methanol was hydrogenated in a stirred autoclave at room temperature and 100 psi overnight. The resulting solution of D-N-acetyl-6-methyltryptophan (81.5% e.e.) was concentrated in vacuo and the solid residue dissolved in 1800 ml of 3% aqueous $NH_3$ at 84°. The slightly turbid solution was filtered and refrigerated overnight. The precipitate was collected, washed with ethanol (−70°) and dried to afford 201.9 g (67%) of product as white crystals, m.p. 216° (dec.); $[\alpha]_D^{25} = -29.4°$ (c=1,$H_2O$); enantiomeric excess: 99%+[1].

[1] The enantiomeric excess was determined by coupling the deacetylated amino acid with L-glutamic acid N-carboxyanhydride and chromatographic separation of the diastereomeric dipeptides on an amino acid analyzer.

The filtrate was acidified with 12 N HCl, the precipitate collected, washed with water and recrystallized twice from 3% $NH_3$ to yield a second crop of product:

41.5 g (14%) of white crystals, m.p. 213° (dec.); $[\alpha]_D^{25} = -29.6°$ (c=1,H$_2$O); enantiomeric excess: 99%+.

EXAMPLE 34

D-6-Methyltryptophan

A mixture of 56.8 g (0.21 mol) of the compound of Example 33 and 600 ml of 2.5 N HCl was heated under nitrogen at 95° for 4 hours. The cooled solution was extracted with methylene chloride and then adjusted to pH 5 with NaOH. The mixture was refrigerated overnight. The precipitate was collected, washed with ice-cold water (100 ml) and dried to give 34.6 g of crude product as beige crystals. A second crop of 5.9 g of product was obtained after concentration of the mother liquor. The combined crops were recrystallized twice from acetic acid and the white acetic acid salt suspended in water (240 ml). The product was collected and dried (100°/0.5 mm) to yield 27.9 g (62%) of D-6-methyltryptophan as white crystals, m.p. 286° (dec) $[\alpha]_D^{25} = 19.8°$ (c=0.4, AcOH); enantiomeric excess 99.5%.

EXAMPLE 35

Alpha-nitro-6-methyl-3-indoleacrylic acid methylester

A mixture of 32.5 g (0.25 mol) of 6-methylindole and 52.5 g (0.30 mol) of α-nitro-β-ethoxyacrylic acid methylester was let stand in a large crystallization dish at room temperature for 20 hours. The brown-orange solid was triturated with ether-hexane 1:1, the crystalline material collected by filtration, washed with ether and dried to afford 44.5 g. (69%) of product as orange crystals, m.p. 167°-169°.

EXAMPLE 36

Alpha-amino-6-methyl-3-indoleacrylic acid methylester hydrochloride 61.7 g (0.24 mol) of α-nitro-6-methyl-3-indoleacrylic acid methylester was converted in the manner described in Example 25 to yield 55.3 g (87%) of product as light tan crystals, m.p. 186° (dec.).

EXAMPLE 37

Alpha-acetamido-6-methyl-3-indoleacrylic acid methylester 53.1 g (0.20 mol) of α-amino-6-methyl-3-indoleacrylic acid methylester hydrochloride was acetylated as described in Example 26 to yield after recrystallization from methanol 37.3 g (69%) of product as light yellow crystals, m.p. 182°-183°.

EXAMPLE 38

D-N-Acetyl-6-chlorotryptophan 5.0 g of degassed α-acetamido-6-chloroindole-3-acrylic acid was slurried with 28 ml of deaereated CH$_3$OH and to this slurry was added 2.0 ml of a solution containing 1.69 mg/ml of a 2.2:1 (weight) mixture of m-tolyl diop and [Rh(1,5-cyclooctadiene) (Cl)]$_2$. Hydrogenation of this slurry for 16 hours at 23° C. with stirring as in Example 43 hereinafter gave a clear solution which on concentration under reduced pressure afforded 5.0 g of D-N-acetyl-6-chlorotryptophan having $[\alpha]_D^{25} = -24.94°$ (c 1.0, CH$_3$OH).

EXAMPLE 39

D-6-Chlorotryptophan 57.3 g of D-N-acetyl-6-chlorotryptophan (81% e.e.) was dissolved in 360 ml of warm acetonitrile and stirred at room temperature for 90 minutes. The precipitated racemic N-acetyl-6-chlorotryptophan was removed by filtration and the filtrate concentrated at vacuo. The residual foam was heated with 600 ml of 2 N hydrobromic acid at 115° for 4 hours. The mixture was concentrated at vacuo and the residue taken up in 300 ml of water. The solution was adjusted to pH 5.5 with sodium hydroxide and the mixture chilled in an ice bath. The precipitate was collected by filtration, washed with water and recrystallized from water to afford 23.5 g (48%) of product as off-white crystals, m.p. 265° (dec.); enantiomeric excess: 99%+.

EXAMPLE 40

3-Dimethylamino-2-(5-benzyloxy-2-nitrophenyl)acrolein

A mixture of 15.0 g (0.062 mol) of 5-benzyloxy-2-nitrotoluene, 13.0 g (0.11 mol) of N,N-dimethylformamide dimethylacetal and 75 ml of dimethylformamide was heated under N$_2$ for 20 hours at 150°. The dark red solution was concentrated at vacuo and the residue taken up in 125 ml of methylenechloride. This solution was added at −5° over 30 minutes to a mixture of 68 ml of a solution of 12.5% phosgene in benzene and 6 g dimethylformamide in 135 ml of methylenechloride (prepared by adding the phosgene solution at −5° to the dimethylformamidemethylenechloride). The mixture was allowed to warm to 0° and 73 ml of water and 18 ml of 1 N potassium carbonate was added. After stirring at 5° for 45 minutes, the aqueous layer was separated and the organic layer extracted with water (500 ml) and 1 N potassium carbonate (150 ml). 20 ml of 4 N sodium hydroxide was added to the combined aqueous solutions and the mixture heated at 95° for 1.5 hour. The mixture was extracted with methylenechloride, the combined extracts dried and concentrated to yield 17.9 g (89%) of product as yellow crystals, m.p. 122°-128°. The analytical sample was prepared by two recrystallizations from methanol: yellow crystals, m.p. 133°-134.5°.

Anal. Calcd. for C$_{18}$H$_{18}$N$_2$O$_4$: C,66.25; H,5.56; N,8.58 Found: C,66.13; H,5.56; N,8.46.

EXAMPLE 41

4-(5-Benzyloxy-2-nitrophenyl)-5-dimethylamino-2-nitro-2,4-pentadienoic acid methylester A mixture of 17.3 g (0.053 mol) of the compound of Example 40 and 6.3 g (0.53 mol) of methyl nitroacetate in 115 ml of acetic anhydride was heated at 95° for 1 hour. The mixture was concentrated, the residue slurried with ether, filtered and washed with ether to give 17.6 g (78%) of red orange crystals, m.p. 158°-165°. Recrystallization from benzene-dimethylformamide afforded 13.4 g (59%) of product, m.p. 179°-181°.

Anal. Calcd. for C$_{21}$H$_{21}$N$_3$O$_7$: C,59.01; H,4.95; N,9.83. Found: 58.97; H,4.95; N,9.77.

EXAMPLE 42

5-Benzyloxy-tryptophan

Following the procedure of Example 19, 5.0 g (0.012 mol) of the product of Example 41 were hydrogenated and worked up to yield 2.0 g (55%) of recrystallized product, m.p. 260° (dec.) which was identical with an authentic sample.

EXAMPLE 43

2.00 g of degassed α-acetamido-6-methylindole-3-acrylic acid monohydrate was slurried with 15 ml of deaereated methanol and to this was added 0.55 ml of a CH₃OH solution containing 0.56 mg/ml of a 2.2.:1 (weight) mixture of 4R,5R-trans-bis-(di-meta-tolyl phosphino methyl)-2,2-dimethyl-1,3-dioxalane (m-tolyl diop) (ex natural tartaric acid) with $\mu,\mu^1$-dichlorobis-($\eta^4$-1,5-cyclooctadiene rhodium (I). The solution was stirred under hydrogen at 23° for 16 hours, during which time the H₂ pressure dropped from 41.5 to 32 psi and the reaction mixture became a clear solution. The reaction vessel was vented and the solvents removed under vacuum to give the crude product as a white glass having the analysis: C, 64.52; H, 6.47; N, 10.50; $[\alpha]_D^{25} = -20.94°$ (c 1.0, CH₃OH). Calculated for N-acetyl-6-methyl tryptophan: C, 64.60; H, 6.20; N, 10.76.

EXAMPLE 44

2.00 g of degassed α-acetamido-6-methylindole-3-acrylic acid methylester was slurried with 15 ml of deaereated methanol and 2 ml of the catalyst solution used in Example 43 was added. The slurry was stirred 16 hours at 23° under an initial pressure of 40 psi of H₂ which dropped to 32 psi. The clear solution which formed was concentrated under reduced pressure to give D-N-acetyl-6-methyltryptophan methylester as an off-white powder having $[\alpha]_D^{25} = -11.27°$ (c=1.00, CH₃OH).

EXAMPLE 45

2.00 g of degassed α-acetamido-6-methylindole-3-acrylic acid ethylester was slurried with 9 ml of deaereated methanol and 1 ml of deaereated H₂O and to this was added 1 ml of a catalyst solution containing 0.952 mg/ml of m-tolyl diop and [Rh(1,5-C₈H₁₂/(Cl)]₂ in 2.2:1 weight ratio. Hydrogenation as in Example 44 gave a clear solution which was vented and cooled with stirring to 5° whereupon there precipitated 1.45 g of D-N-acetyl-6-methyltryptophan ethylester [% enantiomeric excess >99.8 by high pressure liquid chromatography]; $[\alpha]_D^{25} = 11.42°$. [(c 1.0, CH₃OH)].

EXAMPLE 46

Following the procedure of Example 43, α-acetamido-6-methyl-3-indoleacrylic acid was asymmetrically hydrogenated using the rhodium compound of Example 43 and DIOP with R₁₀ and R₁₁ substituted as tabulated below. The enantiomeric excess of the resulting tryptophan is set forth in Table I.

TABLE I

| DIOP $R_{10} = R_{11} =$ | ENANTIOMERIC EXCESS |
|---|---|
| Ph | 73.2% |
| 3-CH₃C₆H₄— | 83.4% |
| 4-CH₃C₆H₄— | 71.6% |
| 3,5-(CH₃)₂C₆H₃— | 86.0% |
| 3,4-(CH₃)₂C₆H₃— | 77.8% |
| 2-CH₃OC₆H₄ | 26.7%(S) |
| 3-CH₃OC₆H₄ | 72.2% |
| 3-ClC₆H₄ | 77.8% |

We claim:

1. A process for preparing a compound of the formula:

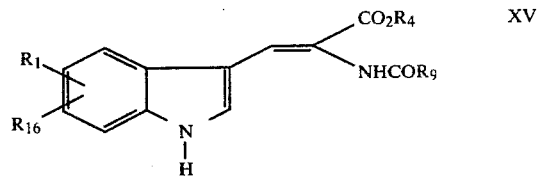

XV wherein R₁ and R₁₆ each are halogen, lower alkyl, hydroxy, lower alkoxy, amino, trihalomethyl or hydrogen, R₄ is alkyl, and R₉ is lower alkyl, hydrogen, halo-lower alkyl or alkoxy, which comprises treating a compound of the formula:

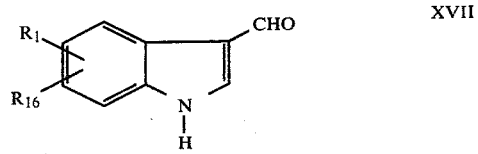

XVII wherein R₁ and R₁₆ are as defined above; with lower acylamidomalonic acid mono(lower alkyl)ester in the presence of a base and a lower alkyl carboxylic acid anhydride.

2. The process of claim 1 wherein the lower acylamidomalonic acid mono(lower alkyl)ester is acetamidomatonic acid monoethyl ester.

3. The process of claim 1 wherein the base is pyridine.

4. The process of claim 1 wherein the lower alkyl carboxylic acid anhydride is acetic anhydride.

5. The process of claim 1 wherein compound XVII is treated with acetamidomalonic acid monoethyl ester in the presence of pyridine and acetic anhydride.

* * * * *